US009150646B2

(12) United States Patent
Thompson et al.

(10) Patent No.: US 9,150,646 B2
(45) Date of Patent: *Oct. 6, 2015

(54) SURFACE-ORIENTED ANTIBODY COATING FOR THE REDUCTION OF POST-STENT RESTENOSIS

(75) Inventors: Michael Thompson, Toronto (CA); Pasquale Benvenuto, Toronto (CA); Christophe Blaszykowski, Toronto (CA)

(73) Assignee: Econous Systems Inc., Toronto, Ontario (CA)

( * ) Notice: Subject to any disclaimer, the term of this patent is extended or adjusted under 35 U.S.C. 154(b) by 1033 days.

This patent is subject to a terminal disclaimer.

(21) Appl. No.: 13/230,036

(22) Filed: Sep. 12, 2011

(65) Prior Publication Data

US 2012/0076833 A1 Mar. 29, 2012

Related U.S. Application Data

(60) Provisional application No. 61/387,684, filed on Sep. 29, 2010.

(51) Int. Cl.
*G01N 33/543* (2006.01)
*C07K 16/28* (2006.01)
*A61K 47/48* (2006.01)
*A61L 31/10* (2006.01)
*A61L 31/16* (2006.01)
*C07K 17/14* (2006.01)
*B05D 1/18* (2006.01)
*B05D 7/14* (2006.01)

(52) U.S. Cl.
CPC ........... *C07K 16/28* (2013.01); *A61K 47/48992* (2013.01); *A61L 31/10* (2013.01); *A61L 31/16* (2013.01); *C07K 17/14* (2013.01); *A61L 2300/256* (2013.01); *A61L 2300/416* (2013.01); *B05D 1/185* (2013.01); *B05D 7/14* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,958,430 A * | 9/1999 | Campbell et al. ............. 424/400 |
| 6,224,099 B1 * | 5/2001 | Nielson et al. ................ 280/741 |
| 8,491,958 B2 * | 7/2013 | Thompson et al. ............ 427/100 |
| 2002/0084429 A1 * | 7/2002 | Craighead et al. ....... 250/492.22 |
| 2002/0182385 A1 * | 12/2002 | Senkevich et al. ............ 428/209 |
| 2002/0182747 A1 * | 12/2002 | Beebe et al. .................. 436/180 |
| 2003/0017936 A1 * | 1/2003 | Yoon et al. ..................... 502/60 |
| 2003/0032071 A1 * | 2/2003 | Wang et al. .................. 435/7.21 |
| 2003/0128043 A1 * | 7/2003 | Zeltz et al. .................... 324/755 |
| 2004/0048270 A1 * | 3/2004 | Zeltz et al. ........................ 435/6 |
| 2004/0081835 A1 * | 4/2004 | Mohry et al. .................. 428/447 |
| 2004/0096849 A1 * | 5/2004 | Klapproth et al. ................ 435/6 |
| 2004/0110009 A1 * | 6/2004 | McGimpsey et al. ....... 428/411.1 |
| 2004/0249227 A1 * | 12/2004 | Klapproth et al. ............. 585/250 |
| 2004/0265889 A1 * | 12/2004 | Durham et al. .................... 435/6 |
| 2005/0118618 A1 * | 6/2005 | Dale ................................. 435/6 |
| 2006/0003438 A1 * | 1/2006 | Engstrom et al. .......... 435/287.2 |
| 2006/0030135 A1 * | 2/2006 | Hu ................................. 438/584 |
| 2006/0093848 A1 * | 5/2006 | Senkevich et al. ............ 428/585 |
| 2006/0147940 A1 * | 7/2006 | Fodor ................................ 435/6 |
| 2007/0042450 A1 * | 2/2007 | McGimpsey et al. ........... 435/14 |
| 2008/0160548 A1 * | 7/2008 | Klapproth .................... 435/7.92 |
| 2008/0202579 A1 * | 8/2008 | Gur et al. ...................... 136/252 |
| 2008/0293592 A1 * | 11/2008 | Ruhe et al. ....................... 506/15 |
| 2009/0123516 A1 * | 5/2009 | Agrawal et al. ............... 424/423 |
| 2009/0325262 A1 * | 12/2009 | Hodneland et al. ........... 435/176 |
| 2011/0136262 A1 * | 6/2011 | Ragavan et al. .............. 436/518 |

OTHER PUBLICATIONS

Balancher et al. "Monolayer Transformation by Nucleophilic Substitution: Applications to the Creation of New Monolayer Assemblies", Langmuir, vol. 6, Nol. 11, 1990.*
Yin et al., "AC133, a Novel Marker for Human Hematopoietic Stem and Progenitor Cells", Blood, vol. 90, No. 12, Dec. 15, 1997, pp. 5002-5012.
Miraglia et al., "A Novel Five-Transmembrane Hematopoietic Stem Cell Antigen: Isolation, Characterization, and Molecular Cloning", Blood, vol. 90, No. 12, Dec. 15, 1997, pp. 5013-5021.
Bird et al., "Single-Chain Antigen-Binding Proteins", http://www.jstor.org/stable/1702600, Oct. 21, 1988, Science, vol. 242, pp. 423-426.
Huston et al., "Protein engineering of antibody binding sites: Recovery of specific activity in an anti-digxin single-chain Fv analogue produced in *Escherichia coli*", Proc. Natl. Acad. Science USA, vol. 85, Aug. 1988, Biochemistry, pp. 5879-5883.
Lu et al., "Oriented Immobilization of Fab Fragments on Silica Surfaces", Analytical Chemistry, vol. 67, No. 1, Jan. 1, 1995, pp. 83-87.
Ward et al., "Binding activities of a repertoire of single immunoglobulin variable domains secreted from *Escherichia coli*", Nature, vol. 341, Oct. 12, 1989, pp. 544-546.

\* cited by examiner

*Primary Examiner* — Ann Lam
(74) *Attorney, Agent, or Firm* — Kathleen E. Marsman; Borden Ladner Gervais LLP

(57) ABSTRACT

A coating for a surface of a surgical implant, the coating including a binding protein for capturing cells to the surface via a bi-functional linker molecule. The linker can have a first functional group (such as a trichlorosilyl group) for covalently linking to the surface, and a second functional group (such as a benzothiosulfonate group) for covalently linking to the binding protein. One exemplary linker molecule is S-(11-trichlorosilyl-undecenyl)benzenethiosulfonate. The coating may be a self-assembled monolayer and may also include a spacer molecule, which can be unreactive with the binding protein. The target cells may be endothelial stem cells (such as endothelial progenitor cells). The binding protein may be an antibody, antibody fragment or non-antibody derived antigen binding molecule. The binding protein may bind a cell surface marker specific to target cell type. Coated surgical implants, and methods of forming such a coating are also contemplated.

7 Claims, 16 Drawing Sheets

SURFACE-ORIENTED ANTIBODY COATING FOR THE REDUCTION OF POST-STENT RESTENOSIS

CROSS REFERENCE TO RELATED APPLICATIONS

This application claims the benefit of priority of U.S. Provisional Patent Application No. 61/387,684 filed on Sep. 29, 2010, which is incorporated herein by reference in its entirety.

FIELD

The present application relates generally to a coating for surgical implants. More particularly, it relates to a coating for surgical implants for capturing cells.

BACKGROUND

One of the leading causes of death worldwide is coronary heart disease. It is commonly instigated by atherosclerosis, which is the deposition of plaque on arterial vessel walls. Such deposition can result in a narrowing (stenosis) of arteries, obstructed and reduced blood flow, and increased risk of heart attack. Angioplasty, a routine surgical procedure, can be performed to widen stenotic arteries. Although successful, angioplasty can suffer from non-uniform arterial widening and re-narrowing (restenosis) due to post-surgical recoil of the artery. To mitigate these shortcomings, stenting can be used as an alternative to angioplasty in suitable candidates.

Stents are expandable meshed cylindrical scaffolds which can be constructed from medical grade stainless steel. They can vary in size from 9 to 23 mm in length, and from 2.5 to 4.0 mm in diameter. Stents can be implanted within the lumen of stenotic arterial vessels in order to widen them and reduce the effects of atherosclerosis. These devices can be implanted as bare metal stents (BMS), or coated with a polymer drug delivery system in drug eluting stents (DES). Despite the advantages of BMS over angioplasty, their function can be limited by complications associated with biocompatibility. For example, post-stent restenosis due to neointimal hyperplasia (cellular hypertrophy, proliferation and deposition of extracellular matrix on the stent and around the site of implantation) remains a difficult challenge.

To combat neointimal hyperplasia (NH), DES employ a polymeric coating that releases anti-proliferative medications. However, concerns regarding delayed healing, late stage thrombosis and hypersensitivity to the polymeric resin continue to surround DES. In light of the challenges that both BMS and DES face, further research into alternative strategies for the reduction of both NH and physiological attack of the stent surface is warranted.

SUMMARY

It is an object to obviate or mitigate at least one disadvantage of previous approaches.

In one aspect, there is provided a coating for a surface of a surgical implant, the coating including a binding protein for capturing cells and a bi-functional linker molecule, wherein the binding protein is linked to the surface of the surgical implant by the bi-functional linker molecule.

The bi-functional linker molecule may include a first functional group for linking to the surface of the surgical implant, and a second functional group for linking to the binding protein. The first functional group may be a trichlorosilyl group for covalently linking to the surface. The second functional group may be a benzothiosulfonate group for covalently linking to the binding protein. The bi-functional linker molecule may be S-(11-trichlorosilyl-undecenyl)benzenethiosulfonate (TUBTS).

The coating may be a self-assembled monolayer (SAM) which includes the bi-functional linker. The SAM may further include a spacer molecule. The spacer molecule may be a silane. The spacer molecule may be hexyltrichlorosilane. The spacer molecule may be shorter than the bi-functional linker. The SAM may include the bi-functional linker and the spacer molecule in a molar ratio of between 90:10 to 30:70 linker to spacer.

The binding protein may bind specifically to a cell surface epitope of the cells. The binding protein may be an antibody, an antibody fragment or a non-antibody derived antigen binding molecule. The binding protein may be an antibody fragment which may be an Fab' fragment (a thiol-containing Fab fragment). The Fab' fragment may be formed through enzymatic digestion of an antibody with a protease which is then followed by a reduction step using an appropriate reducing agent. The protease may be ficin, pepsin or papain.

The cells may be endothelial stem cells.

The cells may be endothelial progenitor cells (EPCs). The binding protein may bind specifically to an epitope which is specific to EPCs.

In another aspect, there is provided a surgical implant including the above-described coating. The surgical implant may be a coronary stent.

In another aspect, there is provided a method for forming a coating on a surface of a surgical implant, the method including the steps of:

forming a self-assembled monolayer (SAM) which includes a bi-functional linker molecule on the surface of the surgical implant; and linking a binding protein for capturing cells to the SAM.

The bi-functional linker molecule may include a first functional group for linking to the surface of the surgical implant, and a second functional group for linking to the binding protein. The first functional group may be a trichlorosilyl group for covalently linking to the surface. The second functional group may be a benzothiosulfonate group for covalently linking to the binding protein. The bi-functional linker molecule may be S-(11-trichlorosilyl-undecenyl)benzenethiosulfonate (TUBTS).

The step of forming a SAM may include treating the surface to form a reactive surface and reacting the first functional group of the bi-functional linker molecule with the reactive surface to form a first covalent bond.

The surface may be a metal surface and treating the surface may include exposing the metal surface to a 95° C. solution having a 3:1 ratio of sulfuric acid to 30% hydrogen peroxide for 30 minutes.

The step of linking the binding protein to the SAM may include reacting an Fab' fragment with the second functional group of the bi-functional linker molecule to form a second covalent bond.

The SAM may include a mixture of the bi-functional linker molecule and a spacer molecule. The spacer molecule may be shorter than the bi-functional linker. The spacer molecule may be unreactive with the binding protein.

Other aspects and features will become apparent to those ordinarily skilled in the art upon review of the following description of specific embodiments of the application in conjunction with the accompanying figures.

BRIEF DESCRIPTION OF THE DRAWINGS

Embodiments will now be described, by way of example only, with reference to the attached Figures, wherein.

DETAILED DESCRIPTION

Coating for Surgical Implants

Figure 1:
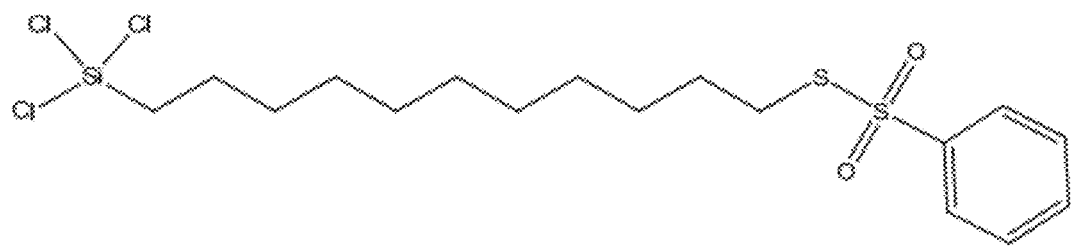
FIG. 1 depicts the molecular structure of one exemplary linker, S-(11-trichlorosilyl-undecenyl)benzenethiosulfonate (TUBTS)

In one aspect of the application, there is provided a coating for a surgical implant.

In one embodiment, the coating comprises a binding protein linked to a surface of the surgical implant by a bi-functional linker molecule. The binding protein can be, for example, an antibody, antibody fragment or a non-antibody derived antigen binding molecule. The binding protein is for capturing cells, for example through binding to cell surface antigens on the cells to be captured. In order to bind the cell surface antigens with the binding protein, the binding protein immobilized to the surface must be oriented properly. To increase binding efficacy, and therefore increase the efficacy of cell capture to the surface, it is desirable to increase the likelihood that the binding protein is immobilized on the surface in an orientation so as to present the antigen binding region to the cell surface antigens on the cells. Increasing the likelihood of proper orientation of the binding protein may be achieved by linking the binding protein using a region of the binding protein which is uniquely reactive and does not interfere with the antigen binding capabilities of the binding protein.

With regard to antibody fragments, one example of a uniquely reactive region which does not interfere with antigen binding capabilities of the antibody fragment is the disulfide bonds in the hinge region of an antibody. These bonds can be accessed, and the antibody fragment generated, by enzymatic cleavage of the antibody to generate Fab' fragments (thiol-containing Fab fragments). The thiol moiety is "uniquely reactive" if there are no other thiol moieties in the Fab' fragment that are located in a position other than opposite to the antigen binding site of the antigen-binding Fab' fragment. Immobilizing the antigen-binding Fab' fragment using a uniquely reactive thiol moiety makes it more likely that the antigen-binding Fab' fragment is properly oriented for binding to the cell surface antigens. The antigen-binding Fab' fragment of the antibody can be formed from an antibody containing accessible disulfide bonds, whose disulfide bonds can be reduced to a free thiol moiety without destroying the antigen binding capabilities of that antibody.

One example of a non-antibody derived antigen-binding molecule is a lectin, i.e. a sugar-binding protein or glycoprotein that is specific for its sugar epitope.

A "uniquely reactive region" of a binding protein is a reactive moiety on the binding protein that is not found in another part of the binding protein, and which can react with the bi-functional linker molecule.

The cells may be endothelial stem cells. The cells may be endothelial progenitor cells (EPCs). The coating may comprise a binding protein for binding EPC cell surface antigens. The binding protein may be an antibody fragment, where the antibody fragment may be an Fab' fragment. The Fab' fragment can be generated through known techniques including, for example, digestion of an antibody with a protease, such as ficin, pepsin, or papain. The protease can be used to generate an F(ab')$_2$ fragment, where the F(ab')$_2$ fragment can be used to generate an Fab' fragment using a reducing agent, such as dithiothreitol (DTT). Fab' fragments can also be generated from recombinant DNA expressing the antibody fragment of interest.

Endothelial cells provide the dynamic lining of blood vessels throughout the body and provide many tissue-specific functions, in addition to providing a nonthrombogenic surface for blood cells and conduit for oxygen and nutrient delivery. They are also mobilized after a myocardial infarction, and function to restore the lining of blood vessels that are damaged during the heart attack. An endothelial stem cell is a stem cell that is capable of maturing into at least mature endothelial cells. The endothelial stem cell may be pluripotent, bipotent, or monopotent. Monopotent endothelial stem cells are also referred to as "endothelial progenitor cells" (EPCs) and are capable of developing into mature endothelial cells. Some studies indicate that EPCs may have their origin in a subpopulation of cells which are sloughed into the bloodstream from the endothelium, yet remain viable and display properties consistent with those of a progenitor cell for the endothelial lineage.

Some EPCs are present in the bloodstream. It may be advantageous to capture them to the surface of a surgical implant because (a) they can participate in the re-endothelialization of injured vascular tissue; (b) they can signal the body to terminate protein and cell adhesion; (c) they can be involved with the inhibition of neointima formation; (d) they can differentiate to become endothelial cells; and/or (e) they can form a closely packed, one-cell thick layer when deposited on surfaces. The benefits of such a coating may include increase in the longevity of the implant without constant drug therapy. Moreover, since EPCs are involved in the re-endothelialization of injured vasculature, an EPC coating could assist in the natural healing of damaged cells as opposed to interrupting this process with various pharmaceutics. Overall, these benefits may reduce the severity of restenosis.

"Capturing cells", as used herein, refers to selective immobilization of cells on a surface through interaction of a binding protein (e.g. antibody, antibody fragment, non-antibody derived antigen binding molecule, binding domain, etc.) linked to the surface with a cell surface molecule (e.g. antigen, epitope, binding domain, etc.) of the target cell. Though the cells are referred to herein as "captured" or "immobilized", a skilled person would appreciate that the cells could still carry out aspects of their normal function.

The target cell surface antigen may be specific to (e.g. specifically expressed by) the target cell population, allowing "selective immobilization" of these cells on the surface. The coating may be for recruiting and selectively immobilizing cells from circulating blood. Here, a skilled person would appreciate that a useful target cell surface antigen need not be exclusively expressed by the target cell population (e.g. in the wider context of an organism), provided that the target cell surface antigen is sufficiently enriched in or unique to the target cells (in the context of the cells in the blood from which the target cells are to be selectively immobilized). A useful target cell surface antigen is "sufficiently enriched" in the target cells if the antigen permits the target cells to be sorted, for example, by fluorescent-assisted cell sorting (FACS) methods, to a population which is at least 80% pure. It may allow purification by FACS to a population that is 85% pure, 90% pure, 95% pure, 96% pure, 97% pure, 98% pure, 99% pure, or substantially 100% pure. The purification may be from whole blood. A useful target cell surface antigen may be one which allows a particular cell lineage to be discerned using known immunohistochemistry and/or fluorescent microscopy techniques.

The term "antigen" refers to an epitope which can be recognized and bound by a binding protein.

The term "epitope" means chemical determinant(s) of an antigen which are capable of specific binding to a binding protein. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

A "binding protein" is a protein which binds to an antigen under physiologically relevant conditions and can be, for example, an antibody, antibody fragment, or a non-antibody derived antigen binding molecule such as a lectin.

Endothelial stem cells are characterized by highly expressed surface antigens. Such antigens include, for example, one or more vascular endothelial growth factor receptors (VEGFR). Examples of VEGFRs include FLK-1 and FLT-1. The FLK-1 receptor is also known by other names, such as VEGFR-2. Human FLK-1 is sometimes referred to in the literature and herein as KDR. At least some endothelial stem cells also express the CD34+ marker. In addition, at least some endothelial stem cells also express the AC133 antigen, which was described by Yin et al. in Blood 90, 5002-5112 (1997) and by Miraglia et al. in Blood 90, 5013-5021 (1997).

The AC133 antigen is expressed on endothelial and hematopoietic stem cells, but not on mature cells. Most, if not all, of the endothelial stem cells express high levels of FLK-1. The CD34 marker is characteristic of stem cells, such as angioblasts and hematopoietic stem cells. Approximately 0.5-10% of CD34+ cells are also FLK-1+. For example, approximately 1% of bone marrow cells are CD34+. Of these, approximately 1% are FLK-1+.

In one embodiment, the binding protein can be surface-oriented and covalently-attached via a bi-functional linker molecule to the surface of the surgical implant.

By "surface-oriented" is meant that the paratope of a binding protein would be positioned so as to be available on the surface of the surgical implant to bind an epitope.

A "bi-functional linker molecule" is a molecule having at least first and second functional groups which are orthogonally reactive. The first and second functional groups are for reacting with first and second molecules, respectively, in order to link them together.

"Link", "linked", "linkage", "linking" as used herein, refer to a chemical linkage between molecules, or the formation thereof. The chemical linkage may be a covalent bond or an indirect link, for instance, through covalent attachment of two molecules via a linker molecule.

"Functional group", as used herein, refers to a particular chemical group or arrangement thereof which is provided on a molecule to impart a specific activity, such as (for example) the ability to react with a target molecule, for example, to form a covalent bond. Though referred to throughout as "bi-functional", a skilled person would appreciate that this descriptor is used, for convenience, to refer to the molecule in both its unreacted and reacted states. As such, coatings described herein as "comprising a bi-functional linker" would be understood to encompass linkers in which the functional groups of the linker have already been reacted with the first and second molecules.

The first functional group is for reacting with a surface in order to anchor the linker. The surface may be a metal surface. The metal may be stainless steel. The first functional group may be for reacting with a hydroxyl group on the surface. The first functional group may be an alkylchlorosilane, or an alkylalkoxysilane, such as triethoxysilane or trimethoxysilane. One specific example of a silyl chloride according to the present application is a trichlorosilyl group, which can react with hydroxyl groups that are present on the specially treated metal surface to form a covalent linkage. The trichlorosilyl group can be reacted with the metal surface to form a self assembled monolayer (SAM).

The second functional group is for reacting with a binding protein. The second functional group may be thiol chemoselective. It may be desirable for the second functional group to be chemically compatible with the first functional group. One specific thiol chemoselective group according to the present application is a benzothiosulfonate group. Benzothiosulfonate is chemically compatible with trichlorosilane in that it does not react with the trichlorosilane functional group. Binding proteins may be covalently linked to the surface by reacting the binding protein with the benzothiosulfonate group of the linker molecule. For instance, benzothiosulfonate may be reacted with a thiol group of an Fab' fragment. Other functional groups which react with thiols, but are not necessarily thiol-specific, may also be used, including esters, disulfides, maleimides, and other types of thiosfulfonates.

FIG. 1 depicts the molecular structure of one exemplary linker (S-(11-trichlorosilyl-undecenyl)benzenethiosulfonate, TUBTS) which is able to form a SAM. TUBTS has a trichlorosilane functional group that bears a trichlorosilyl substrate-anchoring functional group and a benzothiosulfonate functional group, which is thiol chemoselective. Although the TUBTS linker has an 11-carbon chain linking the first and second functional groups, other lengths of carbon chains could be used instead. In some embodiments, the linker can have a shorter carbon chain, for example a chain with 4, 5, 6, 7, 8, 9 or 10 carbon atoms. In other embodiments, the linker can have a longer carbon chain, for example a chain with 12, 13, 14, 15, 16, 17, 18, 19 or 20 carbon atoms. A skilled person would readily be able to identify other linkers able to form SAMs such as, for example, linkers comprising similar functional groups to TUBTS or modifications of the TUBTS structure (e.g. linkers with longer or shorter carbon chains, linkers where the alkyl chain is replaced with an alkenyl chain, an alkynyl chain, or an oligo(ethylene) glycol-based chain, etc.).

Figure 2:
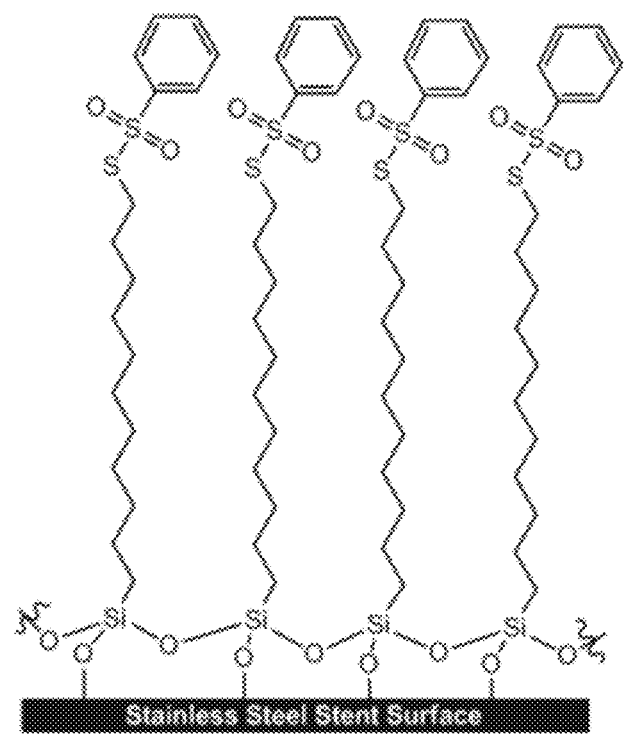
FIG. 2 depicts a simplified self-assembled monolayer (SAM) model of the TUBTS linker.

FIG. 2 depicts a simplified model of a SAM comprising the TUBTS linker, in accordance with one embodiment of the present application.

Binding proteins may be covalently linked to the stent surface through coupling with the benzothiosulfonate functional group of TUBTS. Increasing antigen-binding capacity and/or target cell capture may be influenced by proper orientation and spacing of the binding proteins on the surface. In one embodiment, this may be achieved by enzymatically cleaving an antibody using a protease to generate an Fab' fragment prior to reacting the Fab' fragment with the linker. A protease can be used to generate an $F(ab')_2$ fragment, which can then be used to generate an Fab' fragment using a reducing agent, such as dithiothreitol (DTT). Fab' fragments can also be generated from recombinant DNA expressing the antibody fragment of interest. Ficin, pepsin, or papain are exemplary proteases that may be used to digest an antibody to expose the disulfide bridge in the hinge region of the antibody. The bridge may then be reduced to generate two identical Fab' fragments, each containing a free thiol moiety opposite to the antigen binding site. Since the benzothiosulfonate functional group is thiol-reactive, the Fab' fragments may specifically react with this group in a manner that orients the antigen binding site at the surface so as to increase antigen-binding capacity and/or target cell capture.

In some embodiments, the spatial distribution of the antibodies (or antigen binding molecules) on the surface can be controlled by incorporating a spacer within the SAM. A "spacer molecule", as used herein, refers to a molecule which may be linked to the surface (e.g. of an implant), and which may form part of the SAM. As such, it serves to space apart or "dilute" the bi-functional linker on the surface to which it is attached. In embodiments where the coating includes a spacer molecule, the bi-functional linker can be diluted by the spacer molecule so that the bi-functional linker is 10, 20, 30, 40, 50, 60, 70, 80, or 90 mol % of the SAM. In some embodiments, the spacer molecule does not react, bind or link with the binding protein. In other embodiments, the binding protein is reactive with the spacer molecule, but to a lesser degree than the binding protein is reactive with the bi-functional linker molecule.

A spacer molecule can be chosen based on the bi-functional linker being used. The backbone of the spacer molecule can be based on the backbone, i.e. the chain linking the first and second functional groups in the bi-functional linker, of the bi-functional linker. This can help avoid improper SAM formation resulting from incompatibilities between the backbones of the bi-functional linker and spacer molecules. The spacer molecule can chosen to be shorter than the bi-functional linker in order to avoid steric crowding around the binding protein. The spacer molecule may be a silane. The spacer molecule can be an alkyl trichlorosilane, for example hexyl trichlorosilane (HTS).

A specific coating according to the present application is a coating for a stainless steel surface, where the coating includes a surface-oriented Fab' fragment capable of capturing endothelial progenitor cells (EPCs), where the Fab' fragment is covalently linked to the stainless steel surface by TUBTS.

Surgical Implant

In another aspect of the application, there is provided a surgical implant comprising the above-described coating. The surgical implant can be any surgical implant that would benefit from a coating of cells for improved biocompatibility, and whose surface included chemical groups (e.g. hydroxyl groups) which could react with the bi-functional linker or whose surface could be modified to include chemical groups (e.g. hydroxyl groups) which could react with the bi-functional linker. Examples of materials whose surfaces have chemical groups which could react with the bi-functional linker include stainless steel, aluminum and quartz.

In one embodiment, the surgical implant may be a stent. The stent may be for coronary surgery and may be formed of medical grade stainless steel, such as the material known in the art as AISI 316L.

The SAM-Fab'-coated stent described above may be implanted within the lumen of a stenotic artery where it will capture the EPCs naturally present in the patient's bloodstream.

Method

In another aspect of the application, there is provided a method of forming the above-described coating on a surgical implant.

In one embodiment the method may comprise:
  forming a self-assembled monolayer (SAM) on a metal surface using a bi-functional linker molecule; and
  immobilizing a binding protein on the SAM.

The coated surgical implant could be used directly in surgery to capture EPCs in vivo. Alternatively, the coated surgical implant could be exposed to EPCs prior to implantation, stored as a cell-coated surgical implant, and used in surgery as a cell-coated implant.

In one embodiment, the binding protein may be directed against cell surface antigens of target cells. The target cells can be endothelial stem cells. The endothelial stem cells can be EPCs.

Figure 3:
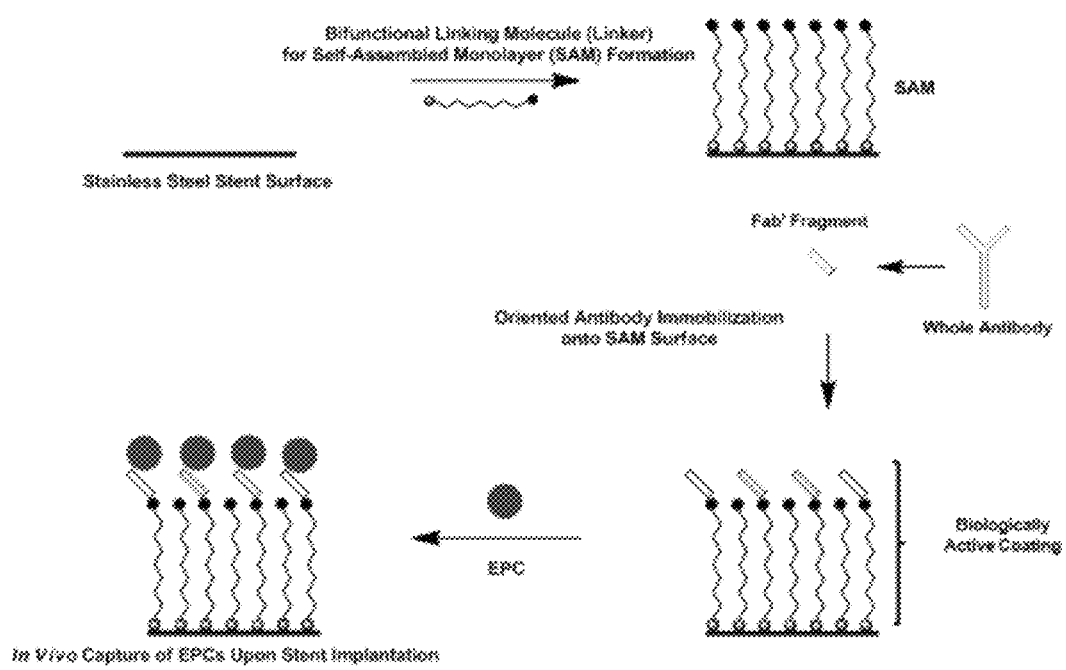
FIG. 3 depicts a protocol for the attachment of endothelial progenitor cells (EPCs) to a stent surface.

FIG. 3 depicts a method according to one embodiment of the application for attaching EPCs to a stainless steel stent surface. This method involves using a bi-functional linker molecule to form a SAM on the surface of stainless steel. The SAM may be formed on a medical grade stainless steel (e.g. AISI 316L) stent. The SAM may be the surface of a coronary stent. The bi-functional linker may comprise a first functional group for reacting with the metal surface in order to form the SAM, and a second functional group for reacting with the binding protein to be immobilized. Thus, the step of "forming" a SAM may comprise covalently linking the bi-functional linker to the surface by reacting the first functional group with the surface. The step of "immobilizing" may comprise covalently linking the binding protein to the bi-functional linker molecule by reacting the binding protein with the second functional group. The binding protein may be an antibody fragment, where the antibody fragment may be an Fab' fragment directed to cell surface antigens of the target cells to be immobilized. A plurality of different binding proteins, directed to a plurality of cell surface antigens, may be used. The target cells may be EPCs. The cell surface markers may be specific to EPCs.

Figure 4:
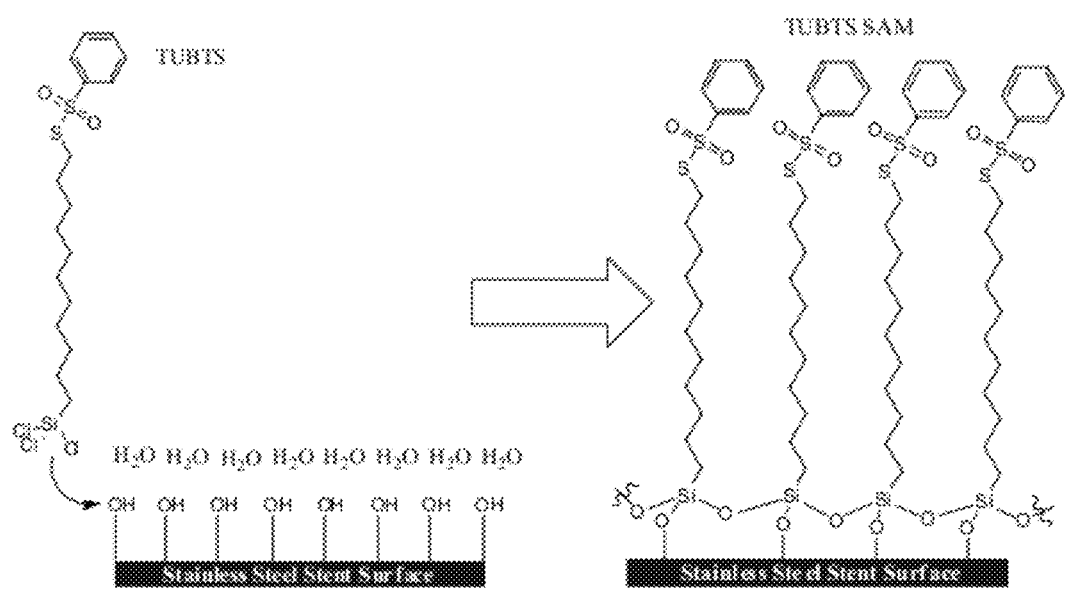
FIG. 4 depicts formation of the SAM using TUBTS.

FIG. 4 depicts formation of the SAM using TUBTS, in accordance with one embodiment of the present application. During SAM formation, the trichlorosilyl moiety of TUBTS may react with a hydroxyl group that is present on the stent surface (which may be specifically treated to form a reactive surface) to form a covalent bond with the stent surface. The treatment of the stent surface can include treatment with solvents of differing polarity (e.g. pentane, acetone, ethanol and/or distilled water) in order to remove weakly bound contaminants. The stent surface can also be treated with a solution having a 3:1 ratio of sulfuric acid to 30% hydrogen peroxide in order to remove strongly bound contaminants and/or previously bound silanes.

Figure 5:
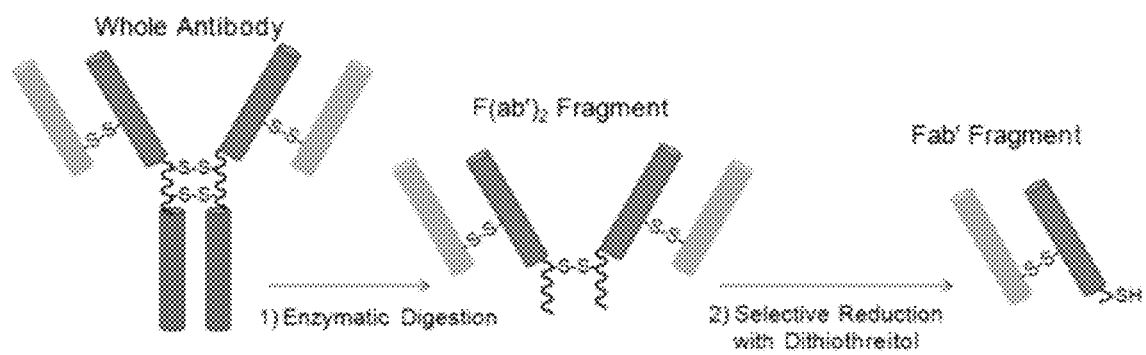
FIG. 5 depicts enzymatic cleavage and modification of a whole antibody to obtain an Fab' fragment.

FIG. 5 depicts enzymatic cleavage and modification of a whole antibody in order to obtain an Fab' fragment. This may be accomplished, for example, by digesting an antibody with ficin, pepsin, or papain to expose the disulfide bridge in the hinge region of the antibody. The bridge may then be reduced to generate two identical Fab' fragments, each containing a free thiol moiety opposite to the antigen binding site.

Figure 6:
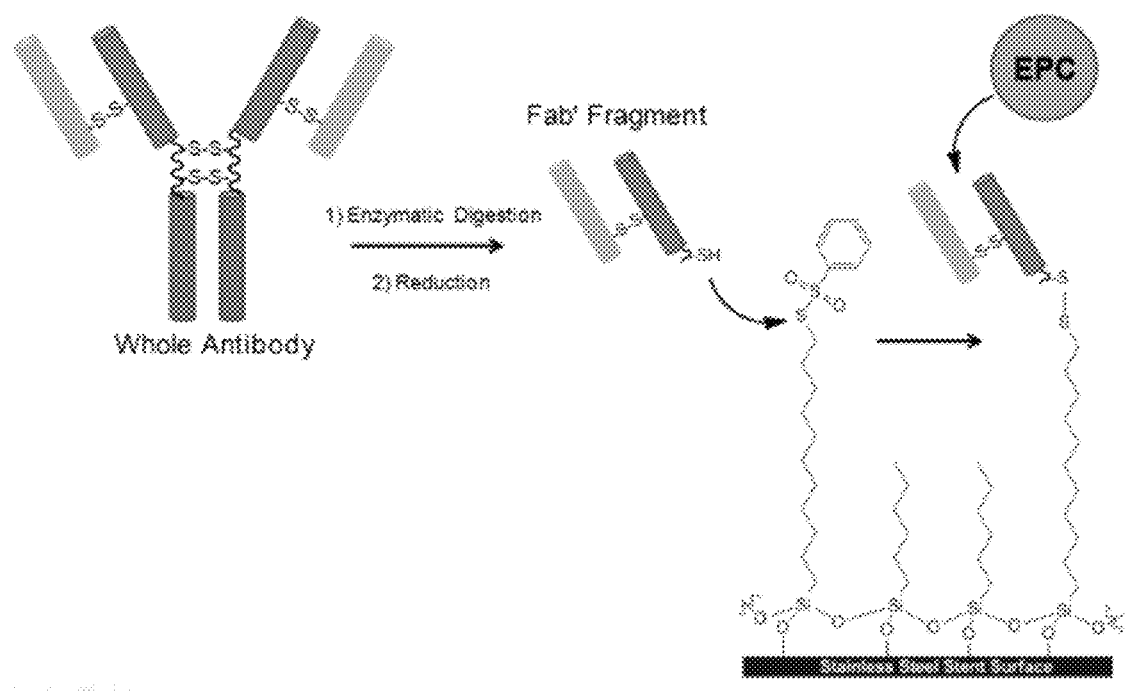
FIG. 6 depicts covalent immobilization of EPC-binding antibody fragments to the TUBTS linker.

FIG. 6 depicts covalent binding of the Fab' fragment to the linker. Since the head group of TUBTS is thiol-reactive, the thiol-containing Fab' fragments may react with the head group in a manner that orients the antigen binding site of the binding protein at the surface such that is available to bind an antigen.

Figure 7:
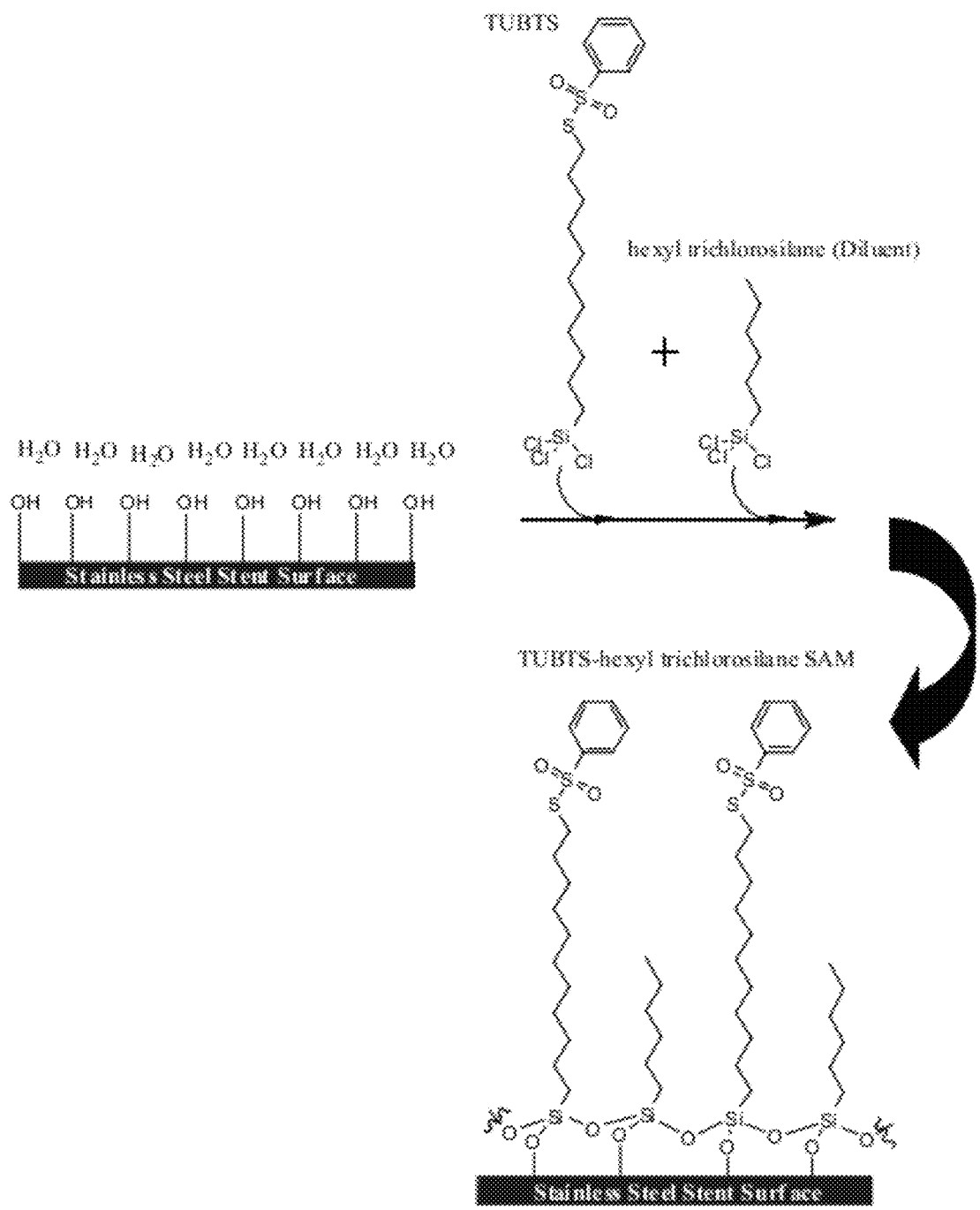
FIG. 7 depicts incorporation of spacer molecules within the SAM.

FIG. 7 depicts one means by which the spatial distribution of the binding proteins on the surface can be controlled, that is by incorporating a spacer molecule within the SAM. Such a spacer molecule may be incorporated within the SAM and may increase the distance between adjacent linker molecules within the SAM. Since the binding protein is immobilized to the surface via bonding with the second functional group of the linker, an increase in separation between linker molecules may result in less steric crowding around the binding protein and a more optimized distance between the binding proteins linked to the SAM.

DEFINITIONS

An "antibody" refers to a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies may be, for example, IgG1, IgG2, IgG3, IgG4, IgM, IgA1, IgA2, IgAsec, IgD, or IgE.

The term "antibody fragment", as used herein, refers to one or more fragments of an antibody that retain the ability to specifically bind to an antigen (e.g. a cell surface antigen of an endothelial progenitor cell, in some embodiments). It has been shown that the antigen-binding function of an antibody can be performed by fragments of a full-length antibody. Examples of binding fragments encompassed within the term "antibody fragments" include (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fab' fragment, an Fab fragment that contains one or more thiol groups from reduction of one or more disulfide bridge in the hinge region; (iv) an Fd fragment consisting of the VH and CH1 domains; (v) an Fv fragment consisting of the VL and VH domains of a single arm of an antibody, (vi) a dAb fragment (Ward et al., (1989) Nature 341:544-546), which consists of a VH domain; and (vii) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antibody fragments". These antibody fragments can be obtained using conventional techniques known to those with skill in the art, and the fragments can be screened for utility in the same manner as are intact antibodies. Terms such as "Fab" and "Fab fragment" are used interchangeably and both refer to the same antibody fragment. For example, in the case of "Fab" and "Fab' fragment", both terms refer to an Fab fragment that contains one or more thiol groups from reduction of one or more disulfide bridge in the hinge region. Similarly, in the case of "F(ab')$_2$" and "F(ab')$_2$ fragment", both terms refer to a bivalent fragment comprising two Fab fragments linked by a disulfide bridge at the hinge region.

The term "antibody", as used herein, is intended to include antibodies having variable and constant regions derived from human and non-human germline immunoglobulin sequences. The antibodies of the application can be chimeric antibodies, that is composite antibodies with portions from each of two species, such as human constant regions and mouse antigen-binding variable regions.

The term "human antibody", as used herein, is intended to include antibodies having variable and constant regions derived from human germline immunoglobulin sequences. The human antibodies of the application may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, "specific binding" and "specifically binds" refers to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to a binding affinity of at least about $10^7$ $M^{-1}$, preferably at least about $10^8$ $M^{-1}$, more preferably at least about $10^9$ $M^{-1}$, and still more preferably at least about $10^{10}$ $M^{-1}$, $10^{11}$ $M^{-1}$, $10^{12}$ $M^{-1}$ or greater, e.g., up to $10^{13}$ $M^{-1}$ or greater. However, "high affinity" binding can vary for other antibody isotypes. For example, "high affinity" binding for an IgM isotype refers to a binding affinity of at least about $1 \times 10^7 M^{-1}$.

EXAMPLES

Stainless Steel Surface Pre-Treatment

Medical grade AISI 316L stainless steel sheets were cut into 5×5 mm square slides. The slides were first polished and then sonicated in various solvents (pentane, acetone, ethanol, distilled water) of differing polarity in order to remove weakly bound contaminants. The slides were then soaked at 90° C., for 30 min, in a solution composed of a 3:1 ratio of sulfuric acid to 30% hydrogen peroxide. The slides were baked in a 190° C. oven for 2 hours. Once baked, they were then nitrogen-plasma cleaned for 5 min. Lastly, the treated steel slides were placed in a humidity chamber at approximately 70% humidity and left to stand overnight on the day prior to SAM formation.

Figure 8:
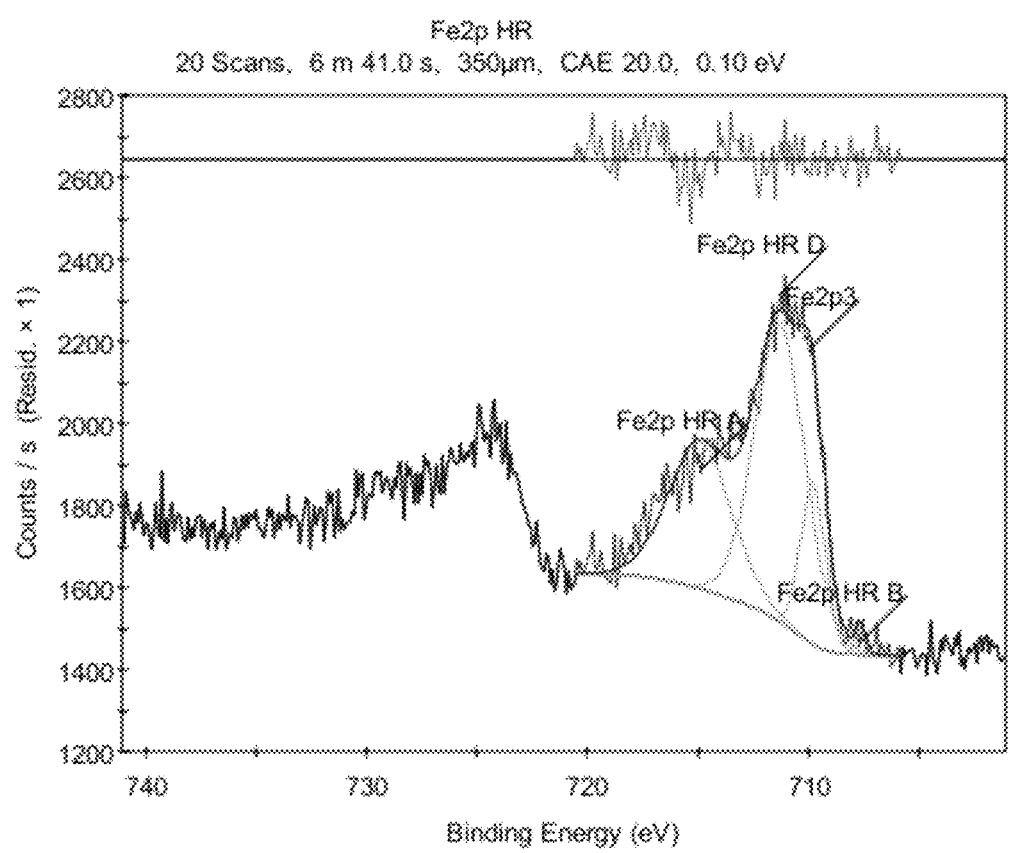
FIG. 8 depicts the iron composition of a steel surface coated with a coating according to the present application using high resolution X-ray photoelectron spectroscopy.
Figure 9:
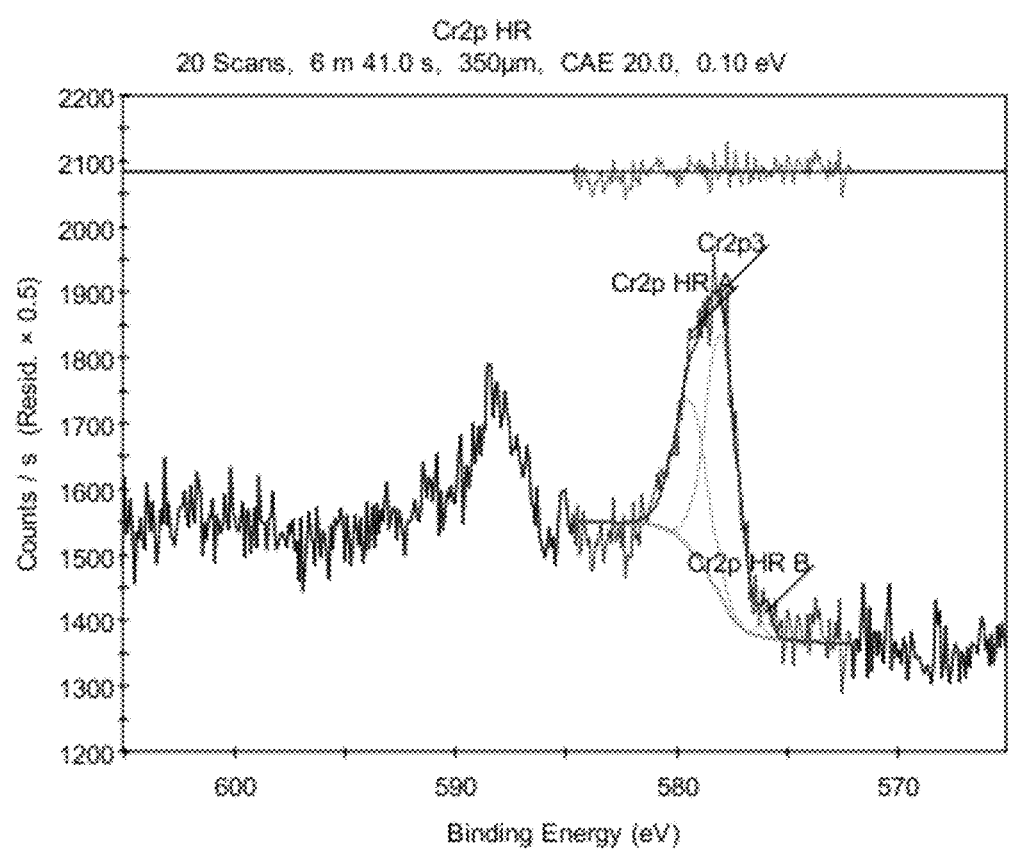
FIG. 9 depicts the chromium composition of the coated steel surface using high resolution X-ray photoelectron spectroscopy.
Figure 10:
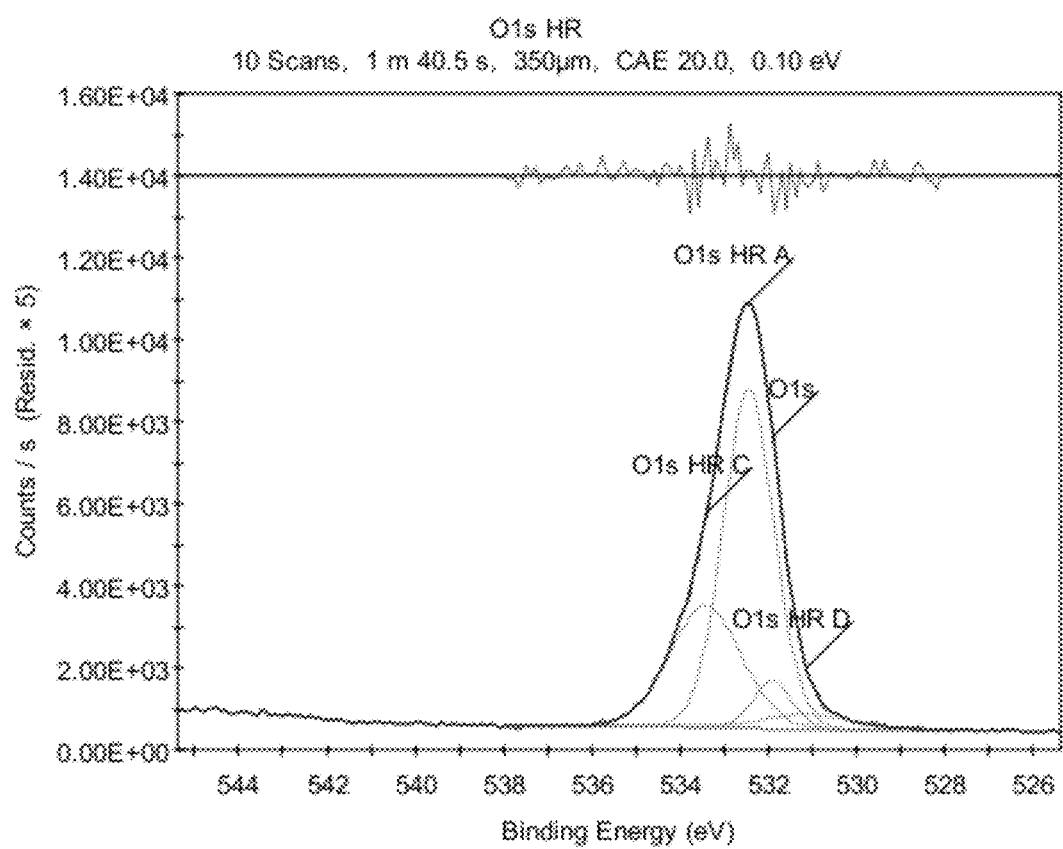
FIG. 10 depicts the oxygen composition of the coated steel surface using high resolution X-ray photoelectron spectroscopy.

High resolution X-ray photoelectron spectroscopy (XPS) was used to analyze the elemental composition of the surface oxide layer of the treated steel surface. The spectra for iron, chromium and oxygen are shown in FIGS. 8, 9 and 10, respectively. Tables 1, 2, and 3, below, show elemental identification and quantification for FIGS. 8, 9 and 10, respectively. Iron and chromium are native constituents of stainless steel. Aside from the expected presence of various chromium and iron oxides, these spectra also show evidence for the existence of surface hydroxyl groups on the treated steel surface. For instance, the 711.27 eV peak in the iron spectrum is indicative of Fe(OH)O and/or $Fe_2O_3$ species, the 577.96 eV peak in the chromium spectrum is indicative of $Cr(OH)_3$ and/or $Cr_2O_3$ species, while the 531.90 eV peak in the oxygen spectrum provides evidence for Fe(OH)O.

Elemental ID and Quantification for FIG. 8

| Name | Peak BE | FWHM eV | Area (P) CPS. eV | At. % | SF |
|---|---|---|---|---|---|
| Fe2p3 | 709.78 | 1.36 | 557.96 | 19.62 | 10.820 |
| Fe2p HR A | 714.90 | 3.49 | 1292.69 | 30.07 | 16.420 |
| Fe2p HR B | 707.63 | 0.53 | 38.43 | 0.89 | 16.420 |
| Fe2p HR D | 711.27 | 2.81 | 2130.30 | 49.42 | 16.420 |

Elemental ID and Quantification for FIG. 9

| Name | Peak BE | FWHM eV | Area (P) CPS. eV | At. % | SF AI Scof |
|---|---|---|---|---|---|
| Cr2p3 | 577.96 | 1.74 | 726.45 | 69.94 | 7.690 |
| Cr2p HR A | 579.36 | 1.90 | 443.71 | 28.18 | 11.670 |
| Cr2p HR B | 575.91 | 0.60 | 29.76 | 1.89 | 11.670 |

Elemental ID and Quantification for FIG. 10

| Name | Peak BE | FWHM eV | Area (P) CPS. eV | At. % | SF AI Scof |
|---|---|---|---|---|---|
| O1s | 531.90 | 1.07 | 1326.67 | 6.48 | 2.930 |
| O1s HR A | 532.44 | 1.41 | 12107.06 | 59.13 | 2.930 |
| O1s HR C | 533.42 | 1.97 | 6110.00 | 29.86 | 2.930 |
| O1s HR D | 531.14 | 2.39 | 930.55 | 4.54 | 2.930 |

Formation of Self-Assembled Monolayers

Following the surface pre-treatment of stainless steel, the stainless steel slides were brought into a glovebox under nitrogen atmosphere for formation of self-assembled monolayers (i.e. "silanization"). Silanization was performed by first dissolving 10 μL of the TUBTS linker in 10 mL of anhydrous toluene. This TUBTS linker solution was then added to a sealable container and a steel slide was submerged in the TUBTS solution and sealed. This container was then removed from the glovebox and placed on a rotator until SAM formation was completed. Once the SAM was formed, the SAM coated stainless steel sample was removed from the container and then rinsed and sonicated in toluene and chloroform to remove unbound TUBTS linker molecules, and to thoroughly dry the coated steel slide. In order to prepare a SAM that contains a spacer molecule (i.e. a diluent), a second solution was prepared by dissolving 10 μL of the spacer molecule in 10 mL of anhydrous toluene. To form a SAM with TUBTS and the spacer molecule, the steel slide is soaked in a solution with a desired ratio of TUBTS linker to spacer molecule.

In order to determine the optimal time (soaking time) required for complete SAM formation, a time variable experiment can be performed in which the SAM-coated steel surface is evaluated after various time points of SAM formation. Evaluation of the SAM-coated surface can be carried out by performing contact angle goniometry (CAG) and low resolution XPS for the SAM-coated steel surface at each time point. CAG provides information concerning the wettability of the SAM-coated surface, while XPS provides elemental composition and abundance (expressed as an atomic percentage) information for the first 10 nm of the sample surface. When the contact angles of the surface are plotted against time, the silanization process can be tracked in terms of the changes in wettability that the surface experiences. When atomic percent values from XPS are plotted against time, silanization can be followed in terms of the compositional changes in the elements characteristics of both the linker and steel surface.

Figure 11:
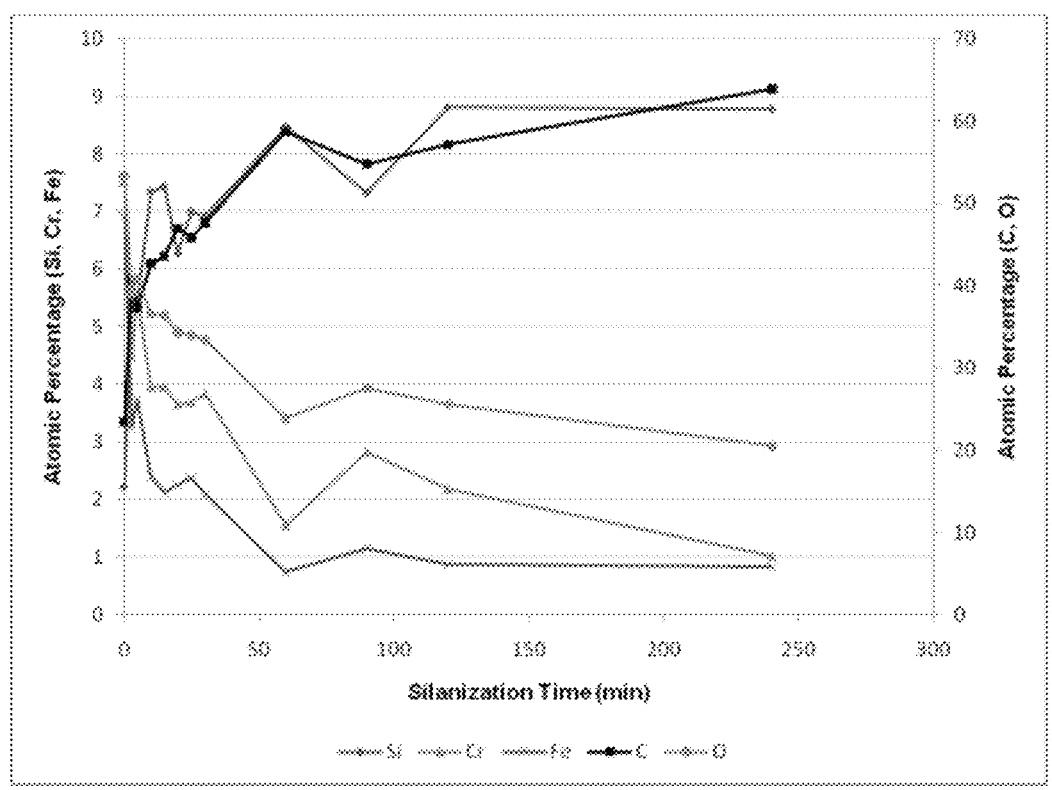
FIG. 11 depicts the elemental composition and abundance of the first 10 nm of steel surfaces coated, for varying lengths of time, with a coating according to the present application using low resolution X-ray photoelectron spectroscopy.
Figure 12:
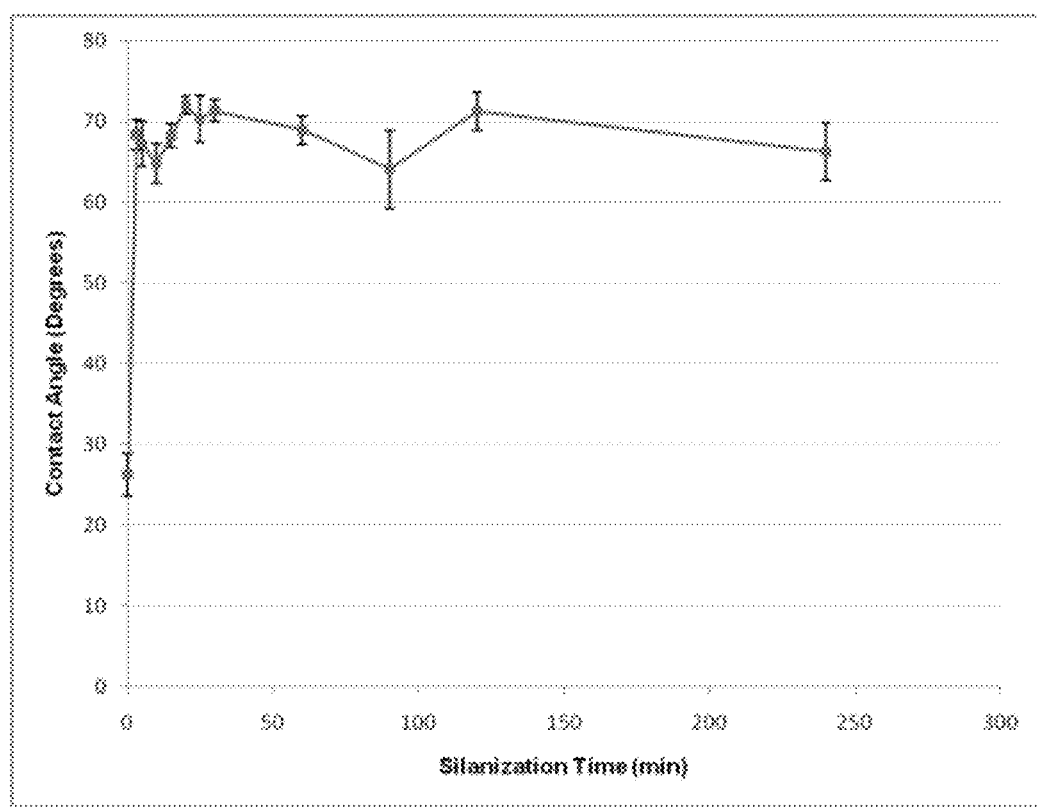
FIG. 12 depicts the wettability of the variably coated steel surfaces using contact angle goniometry.

The time trial experiment was performed in triplicate for TUBTS. Silanization times of 0, 3, 5, 10, 15, 20, 25, 30, 60, 90, 120 and 240 min were investigated. Zero minutes of silanization corresponds to a control steel slide that is pre-treated, but not silanized. The XPS and CAG time trial plots are summarized in FIGS. 11 and 12, respectively. The data points in both of these plots are the mean values of the three replicate experiments. The error bar values in the CAG plot represents the standard deviation. The error bars were omitted from the XPS plot in order to maintain the clarity of the graph.

The XPS time trial plot for TUBTS displays changes in elemental composition that are consistent with general silane SAM formation. For instance, the silicon and carbon content increase from 0 to 60 minutes of silanization, while the chromium, iron and oxygen content all decrease during this same time interval. After 60 min, all elements appear to generally stabilize. The increase in Si and C is reflective of silane deposition since the major source of silicon and carbon originates from the TUBTS solution. As a direct consequence of silane deposition, the changes in iron, chromium and oxygen should be, and are, opposite to those of the silicon and carbon signals. This is because the iron, chromium and majority of the oxygen content are representative of the steel surface. So as the surface is covered with silane, the signals from the steel surface are attenuated and thus result in decreases in the atomic percent of these elements. The stabilization after 60 minutes is likely due to a combination of the surface silane-capacity limit of the steel slide being reached, and the possibility of disorganized multilayer structures.

Similar to the trends found in the XPS plot, the contact angle plot shows a sharp increase between 0 and 3 minutes (the first time point of the trial). From 3 minutes and onwards, the contact angles remain relatively stable. This increase in contact angle is consistent with the deposition of an organic layer on a more hydrophilic surface. Since the TUTBS linker is mainly composed of carbon, this provides further evidence for TUBTS SAM formation on the steel surface. Despite the slight oscillation in the contact angles from 3 to 20 minutes, this data also shows that TUBTS SAM formation on stainless steel begins to occur in as little as 3 minutes.

Overall, the XPS and CAG results show successful TUBTS SAM formation on the treated stainless steel surface. Moreover, SAM formation begins at least as soon as 3 minutes after silanization and continues for at least for 60 or 90 minutes. It may be desirable to form the SAM for the shortest time needed to reach a stable region of the time plot where the Si content is highest. For the TUBTS linker and the treated stainless steel surface, this desirable silanization time is between 3 and 90 minutes. It may be desirable to avoid longer silanization times in order to decrease the possibility of forming disorganized multilayer structures which could have reduced efficiencies for bio-molecular immobilization.

Investigation of TUBTS SAM Reactivity

Figure 13:
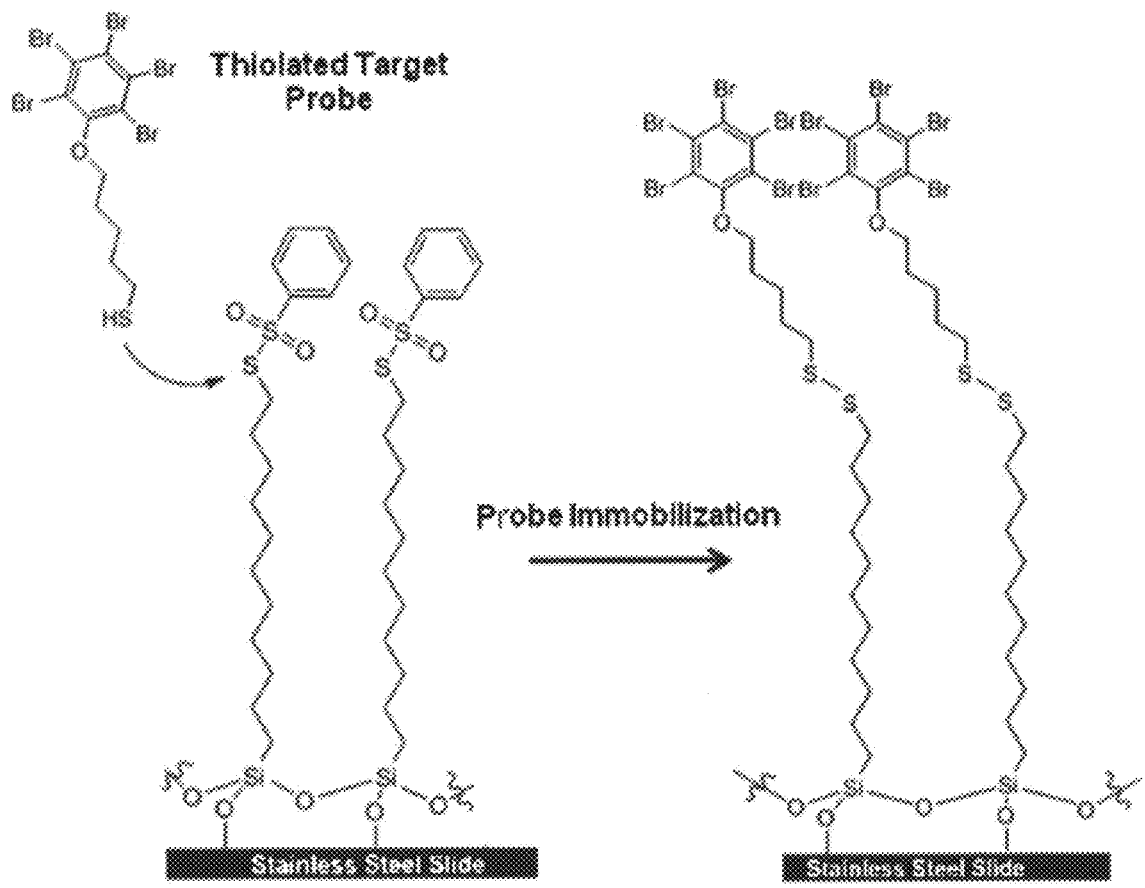
FIG. 13 depicts covalent immobilization of a thiol-containing brominated target probe to the TUBTS linker.

In order to assess the reactivity of the TUBTS SAM, the SAM was reacted with a thiol-containing brominated target probe, as illustrated in FIG. 13. Using low resolution XPS, reaction success was determined by monitoring the abundance of bromine before and after the reaction. Such an experiment was performed to ensure that the prepared SAMs possess the potential for reaction with a thiol-based antibody, antibody fragment or non-antibody derived antigen binding molecule.

The assessment of reactivity was conducted using: (a) a TUBTS SAM that was formed after 90 minutes, and (b) a TUBTS SAM that incorporated the hexyltrichlorosilane (HTS) spacer molecule prepared by soaking a pre-treated slide for 90 minutes in a solution with a 50:50 volumetric ratio of TUBTS:HTS. The ratio of linker (e.g. TUBTS) and spacer (e.g. HTS) in solution may be adjusted to vary the composition of the SAM. These SAMs were individually soaked in a 1 mg/mL solution of probe in dimethylformamide. The SAM coated slides were left to react with the probe overnight to ensure that the reaction reached completion. After the overnight soaking, the slides were removed from the probe solution and rinsed in dimethylformamide and chloroform to remove unbound probe molecules.

Figure 14:
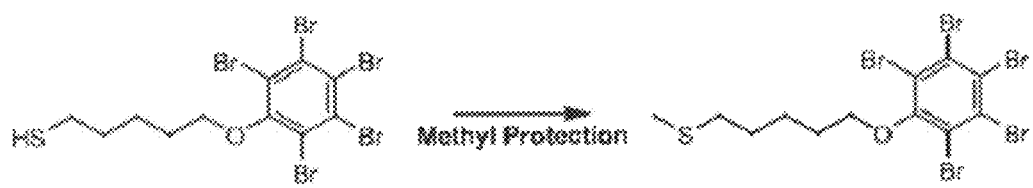
FIG. 14 depicts an unreactive, methyl protected brominated control probe.

Five controls were also prepared: (1) a pre-treated slide that was not silanized with TUBTS, (2) a 90 minute TUBTS SAM that was not exposed to the probe, (3) a TUBTS-HTS SAM that was not exposed to the probe, (4) a treated, but non-silanized steel slide soaked in a solution of the probe overnight, and (5) a 90 minute TUBTS SAM that was soaked overnight in a solution of a methyl protected brominated control probe. The methyl protected control probe, illustrated in FIG. 14, contained a methyl group that prevents the control probe from reacting with the TUBTS SAM. The results are summarized in Table 4, below.

TABLE 4

| Sample | Bromine Atomic Percentage |
|---|---|
| Pre-treated steel slide | 0.20 |
| Pre-treated steel slide exposed to probe | 0.58 |
| TUBTS SAM | 0 |
| TUBTS-HTS SAM | 0.08 |
| TUBTS SAM exposed to probe | 4.4 |
| TUBTS-HTS SAM exposed to probe | 3.3 |

The increase in bromine content only after the SAMs were exposed to the probe clearly demonstrates that the 90 minutes TUTBS and TUBTS-HTS SAMs are reactive towards the probe. The lack of probe immobilization when using the methyl protected probe confirms that (i) the SAMs are reacting with the probe via the thiol group, and (ii) that the non-methyl protected probe is immobilized via a covalent sulfur-sulfur bond. These results also indicate that the orientation of TUBTS within a SAM structure facilitates binding of the probe and that the HTS spacer is not reactive towards this probe. Moreover, as expected, the amount of immobilized probe on the TUBTS-HTS SAM was lower than that found on the TUBTS SAM.

Generation of Fab' Fragments for Immobilization to TUBTS SAMs

Fab' fragments were generated from rabbit F(ab')$_2$ IgG (purchased from SouthernBiotech) according to a modified protocol given by Lu et al. in Analytical Chemistry 67, 83-87 (1995) (Note that to validate the antibody fragmentation and immobilization procedures, rabbit IgG was used as model antibody before work is carried out with the more costly EPC-binding antibodies). In brief, the F(ab')$_2$ sample was diluted from 5 mg/mL to 1.25 mg/mL using a buffer containing 100 mM NaCl, 100 mM borate, 50 mM Citrate and 3 mM EDTA at pH 5.5 (referred to herein as "reduction buffer"). The sample was then dialyzed into the same reduction buffer. Once dialyzed, dithiothreitol (DTT) was added to the 1.25 mg/mL of F(ab')$_2$ sample to a final concentration of 2.5 mM. The reduction was allowed to proceed for 90 minutes at room temperature. After 90 min, the reduced F(ab')$_2$ sample was dialyzed into pH 7.2 phosphate buffered saline (PBS buffer) in order to remove DTT from the sample, and also to better preserve the sample.

Figure 15:
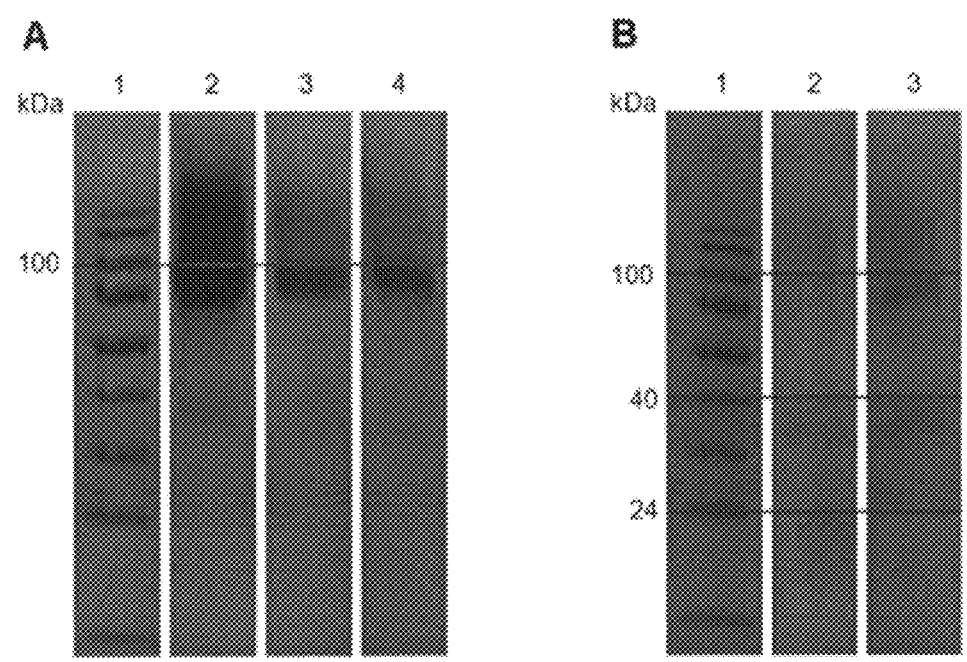
FIG. 15 depicts the SDS-PAGE gel results after each step of the F(ab')$_2$ reduction protocol for the generation of Fab' fragments.

The generation of Fab' fragments according to the aforementioned protocol was monitored by SDS-PAGE gel electrophoresis under non-reducing conditions. The gel results are shown in gels A and B of FIG. 15. In gel A, lane 2, the stock rabbit F(ab')$_2$ IgG band is observed at approximately 100 kDa as expected. In the same gel, it is seen that the F(ab')$_2$ fragment remains intact and unaffected after both dilution (lane 3) and dialysis into the reduction buffer (lane 4). The only change in this gel was a weakening in the intensity of the F(ab')$_2$ band after each treatment. This was due to sample loss throughout the reduction protocol. In gel B, lane 2, two new bands at approximately 40 and 20 kDa appear after the reduction of the F(ab')$_2$ sample. The band at ~40 kDa is suspected of being the Fab' fragment since it is approximately half the size of the F(ab')$_2$ fragment. The band at ~20 kDa are likely fragments of the Fab' fragment due to a combination of over-reduction, and leftover DTT during gel sample preparation (the samples were mixed with a loading buffer and heated prior to being ran on the gel). After dialysis into PBS buffer and removal of DTT (gel B, lane 3), the band at ~20 kDa was barely present while the major and most intense bands were those at approximately 100 and 40 kDa which represented leftover, unreduced F(ab)'$_2$ and the Fab' fragment respectively.

Figure 16:
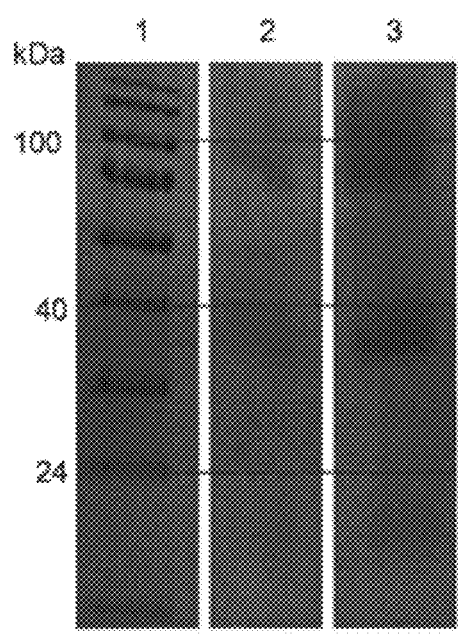
FIG. 16 depicts the SDS-PAGE gel results for the pooled and concentrated Fab' fragment antibody sample for use in Ellman's test for thiols.

To determine if the Fab' fragment was thiolated, several samples of DTT-reduced rabbit F(ab')$_2$ were pooled and concentrated using a centrifuge filter with a 35 kDa molecular weight cut-off in order to obtain enough sample for Ellman's test for thiols. Prior to this test, the pooled and concentrated antibody sample was visualized using non reducing SDS-page gel electrophoresis. The gel picture is shown in FIG. 16. In lane 2 of this gel, three bands were present in the pooled pre-concentrate. The two major and most intense bands were those occurring at approximately 100 and 40 kDa which represented leftover, unreduced F(ab')$_2$, and the Fab' fragment respectively. The third was a weak minor band at approximately 20 kDa which was likely fragments of the Fab' fragment due to over-reduction. When the pooled antibody sample was concentrated (lane 3 of FIG. 16), all three fragment bands present in lane 2 became more intense. This was expected since the concentration of all antibody fragments should increase after the concentration step. The concentrated antibody sample (as shown in lane 3 of FIG. 16) was then used in Ellman's test for thiols. In brief, Ellman's test was performed by reacting dithionitrobenzoic acid (Ellman's reagent) with the antibody sample that contained the Fab' fragment which was suspected of being thiolated. If the sample does in fact contain thiolated species, then one of the two products from this reaction will be thiobenzoic acid which is yellow and absorbs at 412 nm. When the absorbance of the antibody sample was measured at 412 nm after the reaction, there was a strong absorbance peak at this wavelength with an accompanying colour change from clear to yellow which was visually detected. While this test confirmed the presence of thiolated species in the pooled and concentrated antibody sample, it was difficult to determine if the absorbance was entirely due to the Fab' fragment since the antibody sample also contained F(ab')$_2$ and fragments of the Fab'. Despite the impurities of the antibody sample, the only two antibody fragments that should contain thiols would be the Fab' fragment and fragments of the Fab' at approximately 40 and 20 kDa respectively in lane 3 of FIG. 16. Of these two fragments, the Fab' fragment was the dominant fragment (more intense band) as shown in the gel. Moreover, the visual colour change indicated that there was a high concentration of thiolated protein. This, in combination with the band intensities and protein distribution in the gel, suggests that the Fab' fragment was in fact thiolated.

Figure 17:
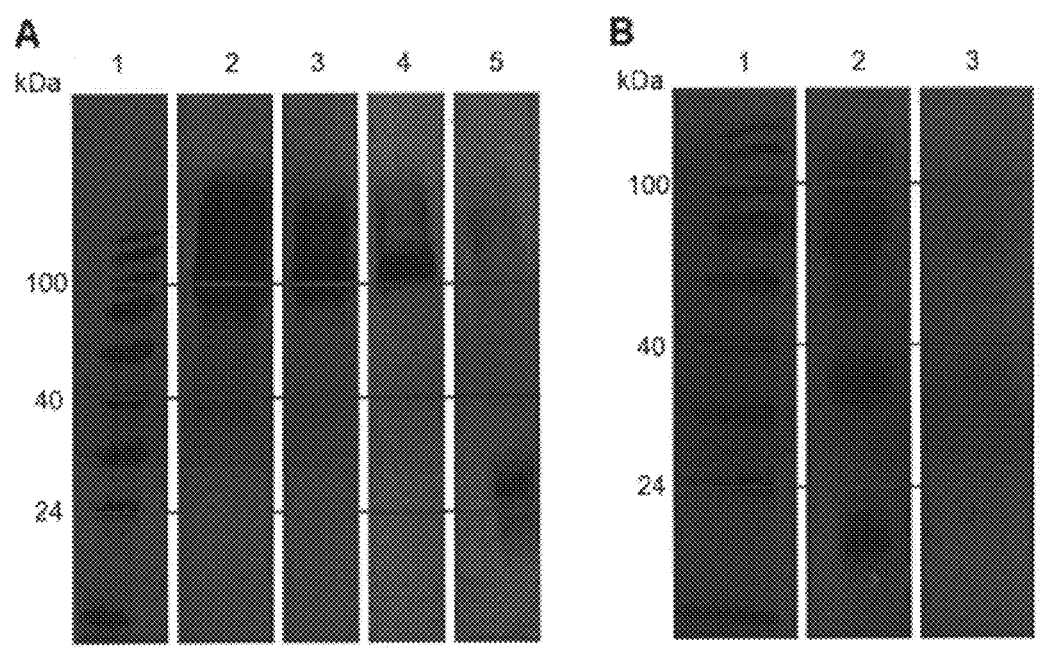
FIG. 17 depicts the SDS-PAGE gel results for the generation of Fab' fragments from freshly ordered rabbit F(ab')$_2$ just prior to the antibody immobilization experiment.

In light of the results from Ellman's test, an immobilization experiment was conducted with newly prepared Fab' fragments from freshly ordered rabbit F(ab')$_2$ IgG. The reduction was performed as previously described and monitored with non-reducing SDS-PAGE gel electrophoresis. The entire reduction process is shown in gels A and B of FIG. 17. In gel A, the results of the F(ab')$_2$ stock IgG, its dilution with the reduction buffer (lane 3), its dialysis into the reduction buffer (lane 4) and the reduction with DTT (lane 5) followed a trend very similar to that observed for the same reduction described above and thus appears to be normal (that is, the band at approximately 100 kDa which corresponds to the F(ab')$_2$ IgG remains intact after each step until the addition of DTT for the reduction and thus fragmentation of the F(ab')$_2$ IgG. The reduction step, as depicted in lane 5 of gel A from FIG. 17, shows three fragment bands at approximately 100, 40 and 20 kDa.). In lane 2 of gel B from FIG. 17, the antibody sample after it has been reduced and been dialyzed into PBS buffer has three fragment bands present; one occurring at ~100 kDa and represents the leftover and unreduced F(ab')$_2$, a second occurring at ~40 kDa that represents the Fab' fragment, and a third band at ~20 kDa that is suspected of being fragments of the Fab' fragment. This sample had to then be diluted by a factor of 7 using PBS buffer in order to produce a sufficient volume of sample for use in the subsequent immobilization experiment. Lane 3 of gel B from FIG. 17 shows the $\frac{1}{7}^{th}$ diluted antibody sample. This sample still contains the same three fragment bands as the undiluted sample after dialysis into PBS buffer. However, the band at ~20 kDa barely appears on the gel and the dominant bands are those corresponding to the F(ab')$_2$ and Fab' fragments.

Figure 18:
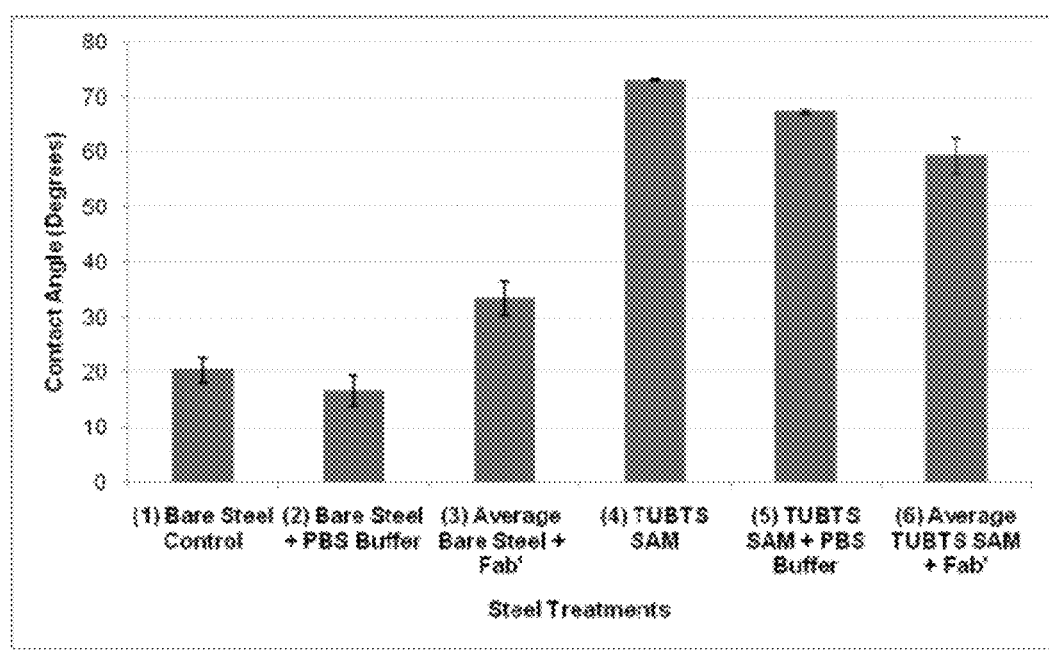
FIG. 18 depicts the change in the surface wettability after each treatment of the antibody immobilization experiment as measured by CAG.

Once the Fab' antibody sample was prepared, ten stainless steel slides were pre-treated according to the protocol described above and received the following six treatments for the immobilization experiment: (1) a pre-treated bare steel slide, (2) a pre-treated bare steel slide soaked in PBS buffer, (3) a pre-treated bare steel slide soaked in the $\frac{1}{7}^{th}$ diluted Fab' antibody solution (treatment was performed in triplicate), (4) a TUBTS SAM-modified steel surface formed after 90 min (according to the protocol described above), (5) a TUBTS SAM-modified steel surface formed after 90 min and soaked in PBS buffer, and (6) a TUBTS-SAM modified steel surface formed after 90 min and soaked in the $\frac{1}{7}^{th}$ diluted Fab' antibody solution (treatment was performed in triplicate). All of the steel slides that received a soak in either PBS, or the $\frac{1}{7}^{th}$ diluted Fab' antibody solution received 1 mL volumes and were allowed to soak over-night at room temperature. These slides were also thoroughly rinsed with PBS buffer and deionised water after the over-night soak and then dried under an N$_2$ stream. The samples were then analyzed by both CAG and low resolution XPS. The CAG results are illustrated in FIG. 18 while the XPS results are summarized Table 5 below:

TABLE 5

| Relative Atomic % | Bare Steel Control | Bare Steel + PBS Buffer | Bare Steel + Fab' Rep. 1 | Bare Steel + Fab' Rep. 2 | Bare Steel + Fab' Rep. 3 | TUBTS SAM | TUBTS SAM + PBS Buffer | TUBTS SAM + Fab' Rep. 1 | TUBTS SAM + Fab' Rep. 2 | TUBTS SAM + Fab' Rep. 3 |
|---|---|---|---|---|---|---|---|---|---|---|
| Carbon | 31.95 | 33.25 | 36.79 | 34.58 | 35.65 | 63.19 | 65.21 | 67.13 | 66.85 | 66.47 |
| Chromium | 8.52 | 8.33 | 7.83 | 8.33 | 7.96 | 0.45 | 0.56 | 0.26 | 0.24 | 0.24 |
| Iron | 5.47 | 4.67 | 3.5 | 5.2 | 4.97 | 0.24 | 0.24 | 0.11 | 0.11 | 0.18 |
| Nitrogen | 2.45 | 2.15 | 2.52 | 2.55 | 2.55 | 0.55 | 0.52 | 10.32 | 10.35 | 10.79 |
| Oxygen | 47.28 | 48.29 | 45.84 | 46.17 | 45.25 | 18.73 | 17.52 | 16.52 | 16.67 | 16.73 |
| Sulfur | 2.64 | 1.97 | 1.89 | 1.85 | 2.08 | 6.56 | 6.7 | 3.07 | 3.02 | 3.05 |
| Silicon | 1.7 | 1.33 | 1.64 | 1.34 | 1.55 | 10.28 | 9.24 | 2.58 | 2.76 | 2.55 |

Figure 19:
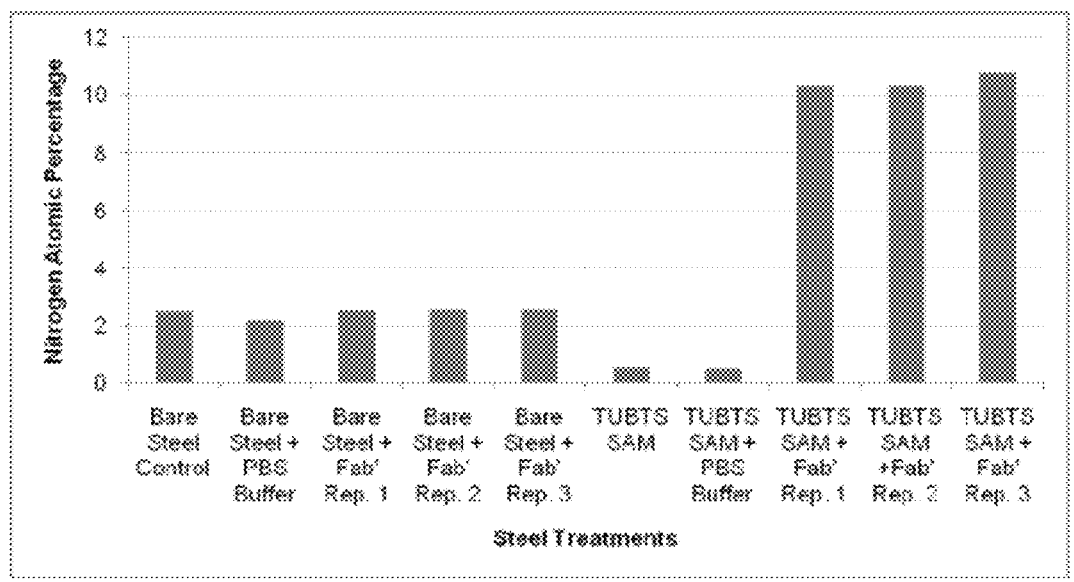
FIG. 19 depicts the change in the relative atomic percentage of nitrogen after each treatment of the antibody immobilization experiment as measured by XPS.

The CAG and XPS results for the pre-treated bare steel slide and the TUBTS SAM formed after 90 min are similar to those obtained in the TUBTS time trial experiment discussed above in the section related to "Formation of Self-Assembled Monolayers". When comparing the pre-treated bare steel to the pre-treated bare steel soaked in PBS buffer, there is very little change in the CAG and XPS results. The same is observed when comparing the TUBTS SAM with the TUBTS SAM after being soaked in PBS buffer. This indicates that the components of the PBS buffer do not adsorb to the surface of the steel and nor do they interfere with the TUBTS SAM. When comparing the CAG results between the bare steel and the bare steel soaked in the Fab' antibody solution, the contact angle rises by 17 degrees after the soak. The same comparison was made between the TUBTS SAM and the TUBTS SAM soaked in the Fab' antibody solution and the contact angle was observed to decrease by 14 degrees after the soaking. Although there was a change in the wettability of the surfaces after exposure to the Fab' antibody solution, it was difficult to determine if the immobilization was successful from the CAG results alone. When examining the preliminary XPS results, the Fab' immobilization to the TUBTS SAM appears to be successful by the dramatic rise in nitrogen from approximately 0.5%, to 10.5% (average of three replicates) only after the TUBTS SAM was exposed to the Fab' antibody solution. The nitrogen signal is indicative of the peptide bond content in the antibody structure. This rise in nitrogen was not observed after the pre-treated bare steel slide is exposed to the Fab' antibody solution. These changes in nitrogen content are summarized in FIG. 19. In addition to the rise in nitrogen, the decreases in sulfur and silicon percentages after exposure of the TUBTS SAM to the Fab' antibody solution also provides evidence for an immobilized species. The decrease in these elements, which are characteristic of a TUBTS SAM, is the result of signal attenuation from an over-layer atop of the TUBTS SAM.

In the preceding description, for purposes of explanation, numerous details are set forth in order to provide a thorough understanding of the embodiments of the application. However, it will be apparent to one skilled in the art that these specific details are not required in order to practice the application. The above-described embodiments of the application are intended to be examples only. Alterations, modifications and variations can be effected to the particular embodiments by those of skill in the art without departing from the scope of the application, which is defined solely by the claims appended hereto.

All references cited herein are incorporated by reference.

What is claimed is:

1. A method for forming a coating on a surface of a surgical implant, the method comprising the steps of:
    forming a self-assembled monolayer (SAM) comprising a bi-functional linker molecule on the surface of the surgical implant; and
    linking a binding protein for capturing cells to the SAM;
        wherein the bi-functional linker molecule is S-(11-trichlorosilyl-undecenyl)benzenethiosulfonate (TUBTS).

2. The method of claim 1, wherein the bi-functional linker molecule comprises a first functional group for linking to the surface of the surgical implant, and a second functional group for linking to the binding protein.

3. The method of claim 2, wherein the first functional group is a trichlorosilyl group for covalently linking to the surface.

4. The method of claim 2, wherein the second functional group is a benzothiosulfonate group for covalently linking to the binding protein.

5. The method of claim 1, wherein the step of forming a SAM comprises treating the surface to form a reactive surface and reacting the first functional group of the bi-functional linker molecule with the reactive surface to form a first covalent bond.

6. The method of claim 5, wherein the surface is a metal surface and treating the surface comprises exposing the metal surface to a 95° C. solution comprising a 3:1 ratio of sulfuric acid to 30% hydrogen peroxide for 30 minutes.

7. The method of claim 2, wherein the step of linking the binding protein to the SAM comprises reacting an Fab' fragment with the second functional group of the bi-functional linker molecule to form a second covalent bond.

* * * * *